United States Patent [19]

Miwa et al.

[11] Patent Number: 4,871,772

[45] Date of Patent: Oct. 3, 1989

[54] PROCESS FOR MAKING A STABLE PHARMACEUTICAL PREPARATION OF PROSTAGLADIN E COMPOUNDS, AND/OR 15R FORMS THEREOF

[75] Inventors: Kohtaro Miwa; Kazuo Igusa; Toshichika Ogasawara, all of Tokyo, Japan

[73] Assignee: Chugai Seiyaku Kabushiki Kaisha, Tokyo, Japan

[21] Appl. No.: 253,902

[22] Filed: Oct. 6, 1988

Related U.S. Application Data

[63] Continuation of Ser. No. 96,824, Sep. 10, 1987, abandoned, which is a continuation of Ser. No. 802,606, Nov. 25, 1985, abandoned.

[30] Foreign Application Priority Data

Nov. 30, 1984 [JP] Japan .................................. 59-253825

[51] Int. Cl.$^4$ .................. A61K 31/19; A61K 31/557; A61K 47/00
[52] U.S. Cl. .................................. 514/573; 514/785; 514/786; 514/970
[58] Field of Search ................. 514/573, 970, 786, 785

[56] References Cited

U.S. PATENT DOCUMENTS

| | | | |
|---|---|---|---|
| 3,450,821 | 6/1969 | Carslensen et al. | 514/970 |
| 3,815,052 | 11/1974 | Monkhouse | 514/573 |
| 3,880,906 | 4/1975 | Spraggins | 560/121 |
| 3,903,297 | 9/1975 | Robert | 514/573 |
| 4,045,577 | 8/1977 | Spraggins | 514/573 |
| 4,092,425 | 5/1978 | Stringfellow | 514/573 |
| 4,335,097 | 6/1982 | David et al. | 514/573 |

FOREIGN PATENT DOCUMENTS 0150732 8/1985 European Pat. Off. ............ 514/573

OTHER PUBLICATIONS

Encyclopedia of Chemical Technology, 3rd edition (1984), pp. 712–714, 738–743.

*Primary Examiner*—Douglas W. Robinson
*Assistant Examiner*—Raymond J. Henley, III
*Attorney, Agent, or Firm*—Browdy and Neimark

[57] ABSTRACT

A process for making a stable pharmaceutical preparation of prostaglandin E compounds and/or 15R forms thereof is diclosed.

Prostagladin E compounds and 15R forms thereof are know to have useful pharmacological actions even if they are used in a vary small amounts. However, they are extremely unstable and, therefore, considerably difficult in application for routine clinical purposes.

In order to remove this difficulty, prostagladin E compounds and 15R forms thereof are formulated into a stable preparation by filling a hard capsule with a solution or a suspension thereof.

8 Claims, No Drawings

PROCESS FOR MAKING A STABLE PHARMACEUTICAL PREPARATION OF PROSTAGLADIN E COMPOUNDS, AND/OR 15R FORMS THEREOF

This application is a continuation of application Ser. No. 096,824, filed 09-10-1987, which is a continuation of application Ser. No. 802,606, filed Nov. 25, 1985 both now abandoned.

The present invention relates to a process for making a stable pharmaceutical preparation of prostaglandin E compounds and/or 15R forms thereof.

Prostaglandin E compounds and 15R forms thereof (hereunder abbreviated as PGEs) exhibit pharmacological actions such as the inhibition of gastric acid secretion, contraction of smooth muscle and the inhibition of blood-platelet aggregation even if they are present in very small amounts. However, PGEs are extremely unstable and inconvenient to handle and, hence, present considerable difficulty in application for routine clinical purposes. Several methods have, therefore, been proposed for stabilizing PGEs and they include: dissolving or mixing PGEs in or with middle-chain aliphatic acid triglycerides (Unexamined Published Japanese Patent Application No. 20304/1982); dissolving PGEs in alkylene glycols or monoesters thereof (Unexamined Published Japanese Patent Application No. 139716/1978); dissolving PGEs in tertiary alcohols of 4–10 carbon atoms (Unexamined Published Japanese Patent Application No. 145515/1975); and dissolving PGEs in vegetable oils and/or acid esters (Unexamined Published Japanese Patent Application No. 105815/1975).

The PGEs thus stabilized by being dissolved or suspended in selected solvents or dispersion media are seldom applied direct to the patient and generally are used for clinical purposes after being formulated in certain dosage forms that can be administered and carried easily. In many cases, PGEs are formulated as soft capsules that are the most commonly used liquid fillable dosage forms in terms of ease of administration and carrying. The problem, however, is that PGEs stabilized by selected solvents or dispersion mediums often lose their stability in soft capsules.

The reason for this phenomenon has not been completely elucidated and, instead, various techniques are currently employed with a view to ensuring the stability of PGEs in soft capsules. For example, in order to ensure complete moistureproofing, expensive packaging efforts are made, or the product is transported or stored cold, or the patient is instructed to always keep the drug in a refrigerator. These partices impose considerable burden on both the manufacturer and the user but have not met with much success in stabilizing PGEs. The present inventors have, therefore, made various studies in order to solve this problem, and found that by filling solutions or dispersions of PGEs not in soft capsules but in hard capsules, the stability of PGEs is significantly improved to such a level that the drug can be handled and stored at room temperature. The present invention has been accomplished on the basis of this finding.

The present invention relates to a process for producing a stable pharmaceutical preparation of prostaglandin E compounds and/or 15R forms thereof by filling a hard capsule with a solution or a suspension of one or more prostaglandins selected from among prostaglandin E compounds and/or 15R forms thereof.

Any hard capsule that complies with the specifications set forth in the Japanese Pharmacopoeia may be used in the present invention. If desired, an enteric hard capsule such as shown in Japanese Patent Public Disclosure No. 42819/1974 may also be used.

After filling with the solution or suspension containing the active ingredient, the cap and body of the hard capsule is desirably sealed with gelatin or other suitable materials in order to prevent leakage of the liquid contents.

Prostaglandin E compounds that may be used as the active ingredient in the present invention include prostaglandin $E_1$ (hereunder abbreviated as $PGE_1$), prostaglandin $E_2$ (hereunder $PGE_2$), 13,14-dihydro-$PGE_1$, 13,14-dihydro-$PGE_2$, 15-methyl-$PGE_1$, 15-methyl-$PGE_2$, 15-methyl-13,14-dihydro-$PGE_1$, 15-methyl-13,14-dihydro-$PGE_2$, 16-methyl-$PGE_1$, 16-methyl-$PGE_2$, 16-methyl-13,14-dihydro-$PGE_1$, 16-methyl-13,14-dihydro-$PGE_2$, 17-methyl-$PGE_1$, 17-methyl-$PGE_2$, 15,16-dimethyl-$PGE_1$, 15,16-dimethyl-$PGE_2$, 16-phenyl-$\omega$-trinol-$PGE_1$, 16-phenyl-$\omega$-trinol-$PGE_2$, 16-phenyl-$\omega$-trinol-13,14-dihydro-$PGE_1$, 16-phenyl-$\omega$-trinol-13,14-dihydro-$PGE_2$, 16-cyclohexyl-$\omega$-trinol-$PGE_2$, 16-cyclohexyl-$\omega$-trinol-$PGE_2$, 16-cyclohexyl-$\omega$-trinol-13,14-dihydro-$PGE_1$, and 16-cyclohexyl-$\omega$-trinol-13,14-dihydro-$PGE_2$, as well as esters and 15R forms thereof.

Any pharmaceutically acceptable solvent or dispersant that is capable of dissolving or dispersing the prostaglandin E compounds listed above and which also is capable of stabilizing the latter may be employed. However, such solvent or dispersant should not interact with the capsule shell to change its properties. Typical examples of a suitable solvent and dispersant are middle-chain triglyceride, glyceryl triacetate, as well as vegetable oils such as peanut oil and sesame oil.

Although the concentration of PGEs in the solution or the suspension may vary broadly a concentration ranging from 0.1 $\mu$g/ml to 100 mg/ml is usually used.

The utility of the present invention will become apparent by reading the following non-limiting Experiment and Examples.

EXPERIMENT

Prostaglandin E compounds each weighing 10 mg were dissolved in tricaprylin or glyceryl triacetate to make a total of 100 g. The solution was divided into portions each weighing 100 mg and charged into soft and hard capsules. The stability characteristics of the resulting PGE capsule preparations are shown in Table 1 below. Each soft capsule shell was composed of 63% gelatin, 29.61% glycerin, 7% purified water, 0.23% methylparaben and 0.06% propylparaben. Capsule No. 4 shown in the Japanese Pharmacopoeia was used as each of the hard capsules.

The percent of active ingredient remained in each capsule after standing at 40° C. for 3 months was determined by the following procedure. Ten capsules were taken and the liquid contents recovered from each capsule were separated by thin layer chromatography on Kieselgel F254 (trademark of E. Merck Co.) using a mixture of chloroform/tetrahydrofuran/glacial acetic acid (10:2:1) as a developing solvent. The silica gel plate was sprayed with an ethanol solution of phosphomolybdic acid, and the light absorbance of each spot was measured with a densitometer. The peak areas of the respective spots were compared to calculate the content of a prostaglandin E in each capsule.

TABLE 1

| No. | Active ingredient | Solvent | Capsule | percent retention after standing 40° C. × 3 mo. |
| --- | --- | --- | --- | --- |
| 1 | $PGE_1$ | tricaprylin | soft capsule | 86.3% |
| 2 | $PGE_1$ | tricaprylin | hard capsule | 99.9% |
| 3 | 15(R)-15-methyl-$PGE_2$ | glyceryl triacetate | soft capsule | 75.8% |
| 4 | 15(R)-15-methyl-PGE | glyceryl triacetate | hard capsule | 99.6% |

The present invention is to be illustrated, but by no means limited, by the following examples.

EXAMPLE 1

Ten milligrams of $PGE_1$ was dissolved in tricaprylin to make a total of 100 g. The solution was divided into portions each weighing 150 mg, which were charged into hard capsules (No. 4 in the Japanese Pharmacopoeia). The cap and body of each capsule was sealed with gelatin.

EXAMPLES 2 TO 11

Stable PGE preparations were prepared as in Example 1 using the active ingredients, solvents (or dispersants) and hard capsule listed in Table 2.

TABLE 2

| Example No. | Active ingredient | Solvent (or dispersant) | Capsule | Charge (mg) |
| --- | --- | --- | --- | --- |
| 2 | $PGE_2$ | glyceryl triacetate | No. 4 capsule in the Japanese Pharmacopoeia | 150 |
| 3 | $PGE_2$ | sesame oil | " | " |
| 4 | 15(R)-15-methyl-$PGE_2$ | glyceryl triacetate | " | " |
| 5 | 15(R)-15-methyl-$PGE_2$ | tricaprylin | " | " |
| 6 | $PGE_2$ methyl ester | tricaprylin | " | " |
| 7 | 15(R)-15-methyl-$PGE_2$ methy ester | glyceryl triacetate | " | " |
| 8 | 15(R)-15-methyl-$PGE_2$ methy ester | peanut oil | " | " |
| 9 | 16-methyl-$PGE_2$ | glyceryl triacetate | " | " |
| 10 | 15,16-dimenthyl-$PGE_2$ | octyldecyl triglyceride | " | " |
| 11 | 15-methyl-13,14-dihydro-$PGE_2$ | octyldecyl triglyceride | " | " |

What is claimed is:

1. A stable pharmaceutical preparation which comprises a hard capsule containing a solution or dispersion of prostaglandin $E_1$ in tricaprylin or 15(R)-15-methyl prostaglandin $E_2$.

2. The pharmaceutical preparation according to claim 1, wherein said prostaglandin is 15(R)-15-methyl-$PGE_2$.

3. The pharmaceutical preparation according to claim 1, wherein said prostaglandin is prostaglandin $E_1$.

4. The pharmaceutical preparation according to claim 1, wherein the concentration of said prostaglandin ranges from 0.1 µg/ml to 100 mg/ml.

5. The pharamceutical preparation according to claim 2, wherein the concentration of said prostaglandin ranges from 0.1 µg/ml to 100 mg/ml.

6. The pharmaceutical preparation according to claim 3, wherein the concentration of said prostaglandin ranges from 0.1 µg/ml to 100 mg/ml.

7. The pharmaceutical preparation according to claim 1, wherein said capsule is sealed with gelatin.

8. A process for making a stable pharmaceutical preparation of prostaglandin $E_1$ and 15(R)-15 methyl prostaglandin $E_2$ comprising the steps of:

filling a hard capsule with a solution or a dispersion of prostaglandin $E_1$ in tricaprylin or 15(R)-methyl-$PGE_2$ in glyceryl triacetate.

* * * * *